United States Patent
Kondo et al.

[11] 4,212,984
[45] Jul. 15, 1980

[54] PROSTAGLANDIN PRECURSORS

[75] Inventors: Kiyosi Kondo, Yamato; Daiei Tunemoto; Teruo Umemoto, both of Sagamihara, all of Japan

[73] Assignee: Sagami Chemical Research Center, Tokyo, Japan

[21] Appl. No.: 862,329

[22] Filed: Dec. 20, 1977

[30] Foreign Application Priority Data

Dec. 27, 1976 [JP] Japan .................. 51-156364
Dec. 27, 1976 [JP] Japan .................. 51-156365
Dec. 27, 1976 [JP] Japan .................. 51-156366
Dec. 27, 1976 [JP] Japan .................. 51-156367

[51] Int. Cl.² ........................................ C07C 177/00
[52] U.S. Cl. ................................ 560/18; 560/9; 560/122; 556/427; 568/43
[58] Field of Search ................. 560/18, 9, 122; 260/586 R, 448.2 B

[56] References Cited

PUBLICATIONS

Derwent Abst. 27789Y/16 J5 1128-941, 27.02.75.

*Primary Examiner*—Paul J. Killos
*Attorney, Agent, or Firm*—Sughrue, Rothwell, Mion, Zinn and Macpeak

[57] ABSTRACT

4-Oxy-6-alkenyl-bicyclo[3.1.0]hexan-2-one compounds represented by the formula (I)

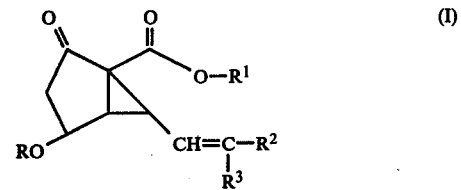

wherein R represents a hydrogen atom or a protective group for a hydroxy group, $R^1$ represents an alkyl group having 1 to 4 carbon atoms or an aryl group, $R^2$ represents a substituted or unsubstituted alkyl group having 1 to 8 carbon atoms and $R^3$ represents a hydrogen atom or an alkyl group having 1 to 4 carbon atoms;

4-oxycyclopentanone compounds represented by the formula (II)

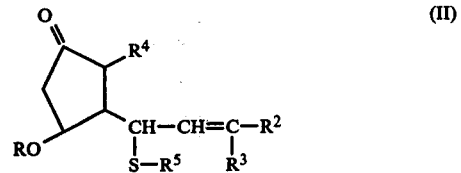

wherein R, $R^2$ and $R^3$ are as defined above, $R^4$ represents a hydroxymethyl group, a methylene group ($=CH_2$) or a —$COOR^1$ group wherein $R^1$ is as defined above, and $R^5$ represents an alkyl group having 1 to 4 carbon atoms or an aryl group, useful as prostaglandin precursors; and processes for preparing the same.

13 Claims, No Drawings

PROSTAGLANDIN PRECURSORS

BACKGROUND OF THE INVENTION

1. Field of the Invention

This invention relates to prostaglandin precursors and processes for preparing the same. More particularly, this invention relates to 4-oxy-6-alkenyl-bicyclo[3.1.0]hexan-2-one compounds represented by the formula (I) hereinafter described and 4-oxycyclopentanone compounds represented by the formula (II) hereinafter described which are useful as precursors for the synthesis of prostaglandin derivatives, and processes for preparing such prostaglandin precursors.

2. Description of the Prior Art

It is well known that the naturally-occurring prostaglandin compounds are composed of 20 carbon atoms and contain in the structure thereof a cyclopentanone ring and exist broadly in the brain, lung, kedney, semen, uterus membrane, etc. of living body. These prostaglandin compounds are also known to have a wide variety of excellent pharmacological activities such as anti-ulcer, hypotensive, anti-asthmatic, uterotonic activities depending upon critical differences in the chemical structure of prostaglandin compounds, and recently the synthesis of prostaglandin compounds has been extensively studied.

Hitherto, in the synthesis of prostaglandin derivatives, the basic cyclopentanone structure is typically formed by (1) a method utilizing Dieckmann reaction as described, for example, in P. S. Pinkney, Or. Synthesis, Coll. Voll., 2, 116 (1943), (2) a method by Claisen condensation of 1,4-dicarbonyl compounds as described, for example, in R. A. Elison, Synthesis, 397 (1973) and (3) a method starting with cyclopentadiene as described, for example, in E. J. Corey et al., J. Amer. Chem. Soc. 93, 1489 (1971).

On the other hand, some of the conventional methods for the synthesis of prostaglandin derivatives employs a bicyclo[3.1.0]hexane compound as an intermediate as described, for example, in W. P. Schneider, Chem. Commun., 304 (1969) and E. J. Corey et al., J. Amer. Chem. Soc., 94, 4014 (1972), but these methods are not considered to be practically useful since the ring-opening of the cyclopropane moiety contained in the above bicyclo[3.1.0]hexane compound takes place only in a low yield and the resulting compound is usually a mixture of diastereomers.

As is well known in the art, the basic structure of prostaglandin derivatives is composed of a cyclopentanone nucleus substituted with an alkyl group or an alkenyl group at the 2- or 3-position of the cyclopentanone nucleus. These side chains were conventionally introduced during the synthesis of prostaglandin derivatives.

More specifically, typical conventional procedures for introducing a side chain at the 3-position of the cyclopentanone nucleus comprise introducing an alkyl or alkenyl group by Michael type addition reaction, as described in C. J. Sih, et al., J. Amer. Chem. Soc., 94, 3643 (1972) and J. H. Fried, J. Amer. Chem. Soc., 94, 9256 (1972), or by reacting a carbonyl group contained in the substituent at the 3-position with a carbon anion to extend a chain length utilizing a carbon-carbon extension reaction, for example, by Wittig reaction, as described in E. J. Corey et al., J. Amer. Chem. Soc., 91, 5675 (1969).

Each of the above conventional processes has certain characteristic features, but is not considered advantageous procedures from the standpoint that it requires expensive and/or dangerous reagents, critical reaction conditions which are very difficult to be controlled, and isolation and purification of the desired product with considerable difficulty, and that the process generally has low selectivity of reaction thereby resulting in low yield of the desired product.

SUMMARY OF THE INVENTION

An object of the present invention is to provide novel 4-oxy-6-alkenyl-bicyclo[3.1.0]hexan-2-one compounds represented by the formula (I)

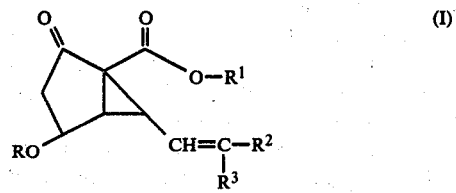

wherein R represents a hydrogen atom or a protective group for a hydroxy group, $R^1$ represents an alkyl group having 1 to 4 carbon atoms or an aryl group, $R^2$ represents a substituted or unsubstituted alkyl group having 1 to 8 carbon atoms and $R^3$ represents a hydrogen atom or an alkyl group having 1 to 4 carbon atoms; and novel 4-oxycyclopentanone compounds represented by the formula (II)

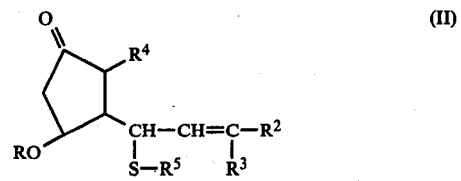

wherein R, $R^2$ and $R^3$ are as defined above, $R^4$ represents a hydroxymethyl group, a methylene group ($=CH_2$) or a $-COOR^1$ group wherein $R^1$ is as defined above, and $R^5$ represents an alkyl group having 1 to 4 carbon atoms or an aryl group.

Another object of this invention is to provide processes for preparing the above 4-oxy-6-alkenyl-bicyclo[3.1.0]hexan-2-one compounds of the formula (I) and 4-oxycyclopentanone compounds of the formula (II).

DETAILED DESCRIPTION OF THE INVENTION

As a result of extensive studies on the process for preparing prostaglandin and anlogues thereof, it was found that the precursors and the processes of the present invention provide expedient means for the synthesis of prostaglandin and derivatives thereof.

The term "alkyl group having 1 to 4 carbon atoms" as used herein for $R^1$, $R^3$ and $R^5$ means a straight or branched chain alkyl group having 1 to 4 carbon atoms and includes, for example, a methyl, ethyl, propyl, isopropyl, n-butyl, sec-butyl or tert-butyl group.

The term "substituted or unsubstituted alkyl group having 1 to 8 carbon atoms" as used herein for $R^2$ means a straight or branched alkyl group having 1 to 8 carbon atoms and includes, in addition to the examples of the alkyl group having 1 to 4 carbon atoms given above, a pentyl, hexyl, heptyl, octyl groups which may be substituted with an —O-alkyl group or a —S-alkyl group wherein the alkyl moiety can be a straight or branched chain and has 1 to 4 carbon atoms, or a phenoxy group which may be substituted with a halogen atom or an alkyl group having 1 to 4 carbon atoms.

The term "aryl group" as used herein for $R^1$ and $R^5$ means an unsubstituted or substituted phenyl group wherein the the substituent is a halogen atom, an alkyl or alkoxy group having 1 to 4 carbon atoms.

The term "halogen" as used herein includes fluorine, chlorine, bromine and iodine.

The term "protective group for a hydroxy group" as used herein for R and $R^6$ refers to protective groups which are generally used for protecting a hydroxy group and which are well known in the art. Typical examples of such protective groups are a tetrahydropyranyl group, a tri(lower alkyl)silyl group, a benzyl group, an alpha-lower alkoxy-lower alkyl group, a lower alkanoyl group, a benzoyl group, etc.

The 4-oxycyclopentanone compounds of the formula (II) include the compounds represented by the following formulae (IIa), (IIb) and (IIc):

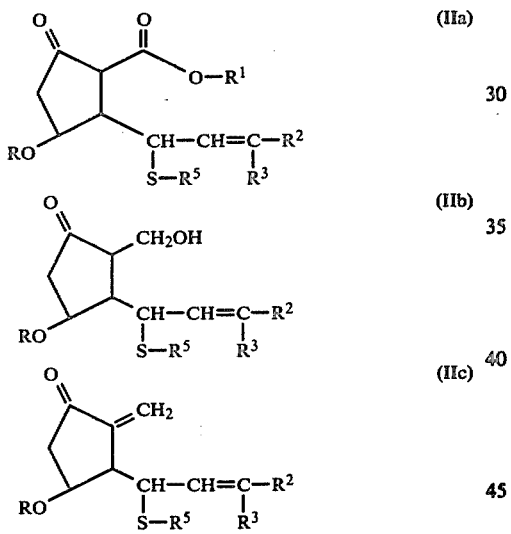

The 4-oxy-6-alkenyl-bicyclo[3.1.0]hexan-2-one compounds of the formula (I) and 4-oxycyclopentanone compounds of the formula (II) of the present invention can be prepared according to the following Reaction Scheme:

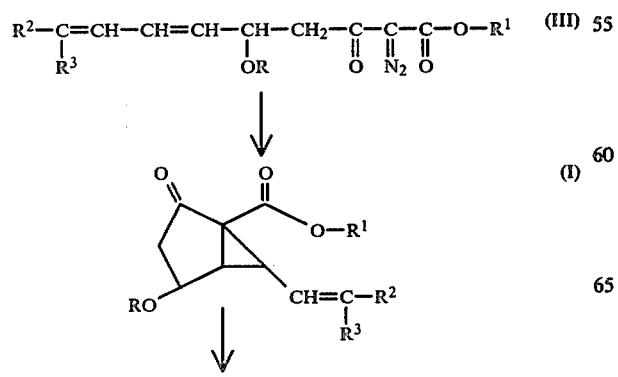

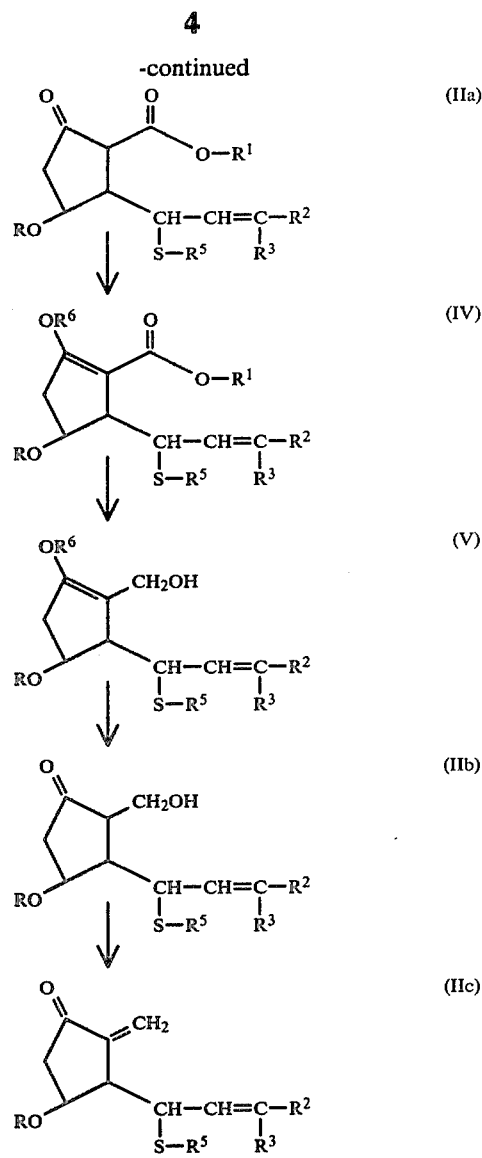

wherein R, $R^1$, $R^2$, $R^3$ and $R^5$ are as defined above and $R^6$ represents a protective group for a hydroxy group.

The present invention provides a process for preparing a 2-methylene-4-oxycyclopentanone compound of the formula (IIc)

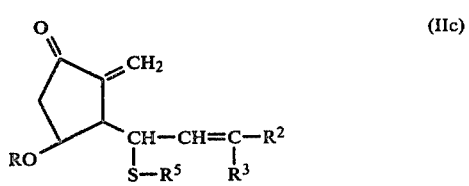

wherein R represents a hydrogen atom or a protective group for a hydroxy group, $R^2$ represents a substituted or unsubstituted alkyl group having 1 to 8 carbon atoms, $R^3$ represents a hydrogen atom or an alkyl group having 1 to 4 carbon atoms and $R^5$ represents an alkyl group having 1 to 4 carbon atoms or an aryl group, which comprises subjecting an α-diazo-β-keto ester compound of the formula (III)

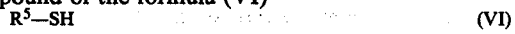 (III)

wherein R, R² and R³ are as defined above and R¹ represents an alkyl group having 1 to 4 carbon atoms or an aryl group, to a carbene or carbenoid formation either by a catalytic reaction or a photo-decomposition to produce a 4-oxy-6-alkenylbicyclo[3.1.0]hexan-2-one compound of the formula (I)

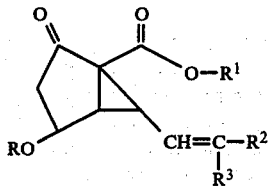 (I)

wherein R, R¹, R² and R³ are as defined above, reacting the thus obtained 4-oxy-6-alkenyl-bicyclo[3.1.0]hexan-2-one compound of the formula (I) with a mercaptan compound of the formula (VI)

R⁵—SH  (VI)

wherein R⁵ is as defined above, in the presence of a base to produce a 4-oxy-2,3-disubstituted-cyclopentanone sulfide compound of the formula (IIa)

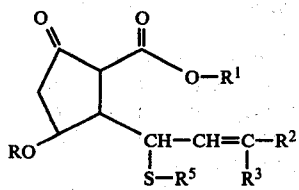 (IIa)

wherein R, R¹, R³ and R⁵ are as defined above, protecting the carbonyl group of the thus obtained 4-oxy-2,3-disubstituted-cyclopentanone sulfide compound with a protective group to produce an enol ether compound of the formula (IV)

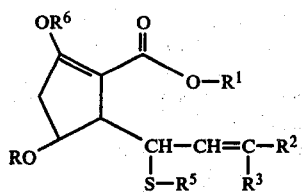 (IV)

wherein R, R¹, R², R³ and R⁵ are as defined above, and R⁶ represents a protective group for a hydroxy group, reducing and thus obtained enol ether compound of the formula (IV) with a reducing agent to produce a compound of the formula (V)

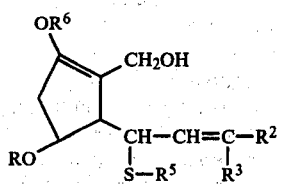 (V)

wherein R, R², R³, R⁵ and R⁶ are as defined above, hydrolyzing the thus obtained compound of the formula (V) to produce a compound of the formula (IIb)

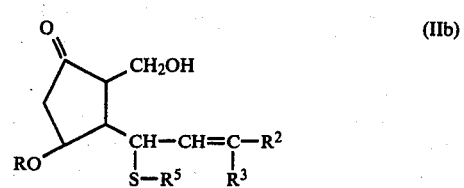 (IIb)

wherein R, R², R³ and R⁵ are as defined above, and treating the resulting compound of the formula (IIb) with a sulfonic acid halide in the presence of a base.

Also, the present invention provides a process for preparing a compound of the formula (I)

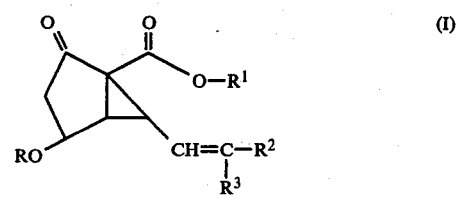 (I)

wherein R, R¹, R² and R³ are as defined above, which comprises subjecting an α-diazo-β-keto ester compound of the above formula (III) to a carbene or carbenoid formation either by a catalytic reaction or a photo-decomposition.

The 4-oxy-2,3-disubstituted-6-alkenyl-bicyclo[3.1.0]-exan-2-one compounds of the present invention having the formula (I) have an ester group at the 1-position and a carbonyl group at the 2-position and thus the cyclopropane ring of the compounds can easily be opened when these compounds are reacted with a nucleophilic reagent to produce selectively the corresponding 4-oxycyclopentanone compound having the formula (IIa).

Occasionally, in the ring-opening and addition reaction between a vinyl-substituted cyclopropane compound and a nucleophilic reagent, the unsaturated double bond of the vinyl moiety usually takes part in the reaction thereby giving rise to a so-called conjugated addition product, as described in J. M. Stewart et al., J. Org. Chem. 34, 7 (1969). However, in accordance with the process of this invention, it was found that the alkenyl group attached to the 6-position of the bicyclo compound of the formula (I) does not affect the above ring-opening and addition reaction thereby producing a 4-oxycyclopentanone compound of the formula (IIa).

The 4-oxycyclopentanone compounds of the formula (IIa) are very useful as precursors for producing prostaglandin compounds since they possess all the functional groups required for converting into prostaglandin compounds, i.e., an ester group at the 2-position and an allylic sulfide group at the 3-position of the cyclopentane ring.

For example, the ester group of the 4-oxycyclopentanone compounds of the formula (IIa) can be transformed to the methylene moiety of 2-methylene-4-oxycyclopentanone compounds of the formula (IIc), which are useful as precursors for synthesis of prostaglandin compounds, as illustrated hereinafter in detail for the production of the formula (IIc). That is, the methylene group attached to the 2-position of the cyclopentane ring can be utilized for the formation of α-chain of prostaglandin compounds since the methylene group functions as an acceptor in the Michael-type addition reaction and thus makes it possible to attain the carbon-carbon extension by reaction with a wide variety of nucleophilic reagents, as described in, for example, G. Stork et al., J. Amer. Chem. Soc., 97, 4745 (1975).

The allylic sulfide group of the 4-oxycyclopentanone compounds represented by the formula (II) can be converted into an allylic alcohol group which is essential for the ω-chain of prostaglandins, via oxidation and rearrangement, as described in, for example, K. G. Untch et al., J. Amer. Chem. Soc., 96, 6774 (1974).

Thus, the above characteristic features of the compounds of this invention and the processes of this invention can provide ideal synthetic procedures for producing side chains attached to cyclopentanone ring of the prostaglandin compounds.

The processes according to the present invention are further illustrated below in greater detail.

The starting material of the formula (III) used in the present invention, α-diazo-β-keto esters, can easily be prepared from commercially available raw materials such as acetoacetic acid esters and dientyl aldehydes according to the method as described in, for example, L. Weiler et al., Tetrahedron Letters, 4835 (1971). For Example, methyl acetoacetate can be reacted with trans, trans-2,4-decadienal to form methyl 5-hydroxy-3-oxotrans, trans-6,8-tetradecadienoate. The resulting β-keto ester compound is then diazotized with a diazotizing agent in the presence of a base to form the desired α-diazo-β-keto esters of the formula (III)

Typical examples of β-keto esters which can be used in preparing the starting material (III) are methyl 5-hydroxy-3-oxo-6,8-tetradecadienoate, ethyl 5-hydroxy-3-oxo-6,8-tetradecadienoate, t-butyl 5-hydroxy-3-oxo-6,8-tetradecadienoate, methyl 5-hydroxy-3-oxo-6,8-tridecadienoate, methyl 5-hydroxy-3-oxo-6,8-pentadecadienoate, methyl 5-benzyloxy-3-oxo-6,8-tetradecadienoate, methyl 3-oxo-5-trimethylsiloxy-6,8-tetradecadienoate, methyl 3-oxo-5-(2-tetrahydropyranyloxy)-6,8-tetradecadienoate, methyl 5-(1-ethoxyethyloxy)-3-oxo-6,8-tetradecadienoate, methyl 5-(1-methoxy-1-methylethyloxy)-3-oxo-6,8-tetradecadienoate, methyl 5-hydroxy-9-methyl-3-oxo-6,8-tetradecadienoate, methyl 5-hydroxy-10-methyl-3-oxo-6,8-tetradecadienoate, methyl 9,10-dimethyl-5-hydroxy-3-oxo-6,8-tetradecadienoate, methyl 5-hydroxy-3-oxo-10-phenoxy-6,8-decadienoate and the like.

Suitable examples of diazotizing agents which can be used in the above diazotization are azide compounds such as tosyl azide, benzenesulfonyl azide, phenyl azide, azidoformate and the like which are well known in the art.

Suitable examples of basic compounds which can be used in the above diazotization reaction are alkali metal hydroxide such as sodium hydroxide, potassium hydroxide and the like, alkali metal alkoxides such as sodium methoxide, sodium ethoxide, sodium t-butoxide, potassium t-butoxide and the like, and organic amines such as triethylamine, tributylamine, dimethylaniline, pyridine, piperidine and the like. Such basic compounds can preferably be used in an equimolar amount relative to the compound to be diazotized.

The diazotization reaction can be carried out in the absence of a solvent, but in order to produce the desired starting materials of the formula (III) in a high yield, it is preferred to use an inert organic solvent such as acetonitrile, dimethylformamide, tetrahydrofuran, alcohols, e.g., methanol, ethanol and the like, ethers, e.g., diethyl ether and the like, and halogenated hydrocarbons such as methylene chloride and the like. The diazotization generally proceed smoothly at room temperature (about 15° to 30° C.) without heating or cooling under atmospheric pressure.

The 4-oxy-6-alkenyl-bicyclo[3.1.0]hexan-2-one compounds (I) can be prepared by subjecting an α-diazo-β-keto ester compound of the formula (III) to carbene or carbenoid formation conditions by taking advantage of an intramolecular addition of the compound of the formula (III).

Generally, in carbene formation by decomposition of such diazo compounds, various reactions may occur and hence the reaction product can be expected to be a mixture of different products, but in accordance with the process of this invention, it is found that the compound of the formula (III) can be selectively converted into the desired 4-oxy-6-alkenyl-bicyclo[3.1.0]hexan-2-one compounds of the formula (I).

The carbene or carbenoid formation can be achieved by either (1) a catalytic method or (2) a photodecomposition method.

The catalytic method can be achieved by catalyzing the starting material of the formula (III) in a trace amount of a catalyst such as a metal or a metal salt, for example, copper powder, copper bronze, copper halides, copper sulfate, acetylacetonate-copper, copper phosphine complex, silver oxide, silver nitrate and the like, in an inert atmosphere thereby obtaining a corresponding carbenoid.

The photodecomposition method can be achieved by exposing the starting material of the formula (III) to the light directly or through an inert atmosphere thereby obtaining a corresponding carbene. The light sources which can be used in the photodecomposition can be those usually employed in chemical industries, for example, low-pressure or high-pressure mercury lamps.

In both catalytic and photodecomposition methods, a solvent is not necessarily required, but the above methods can preferably be conducted using a solution of the starting material of the formula (III) in an inert solvent and in an inert atmosphere in order to minimize the formation of byproducts and to improve the reaction selectivity to the desired product. Typically, the above methods can be advantageously carried out in an inert atmosphere such as nitrogen or argon gas and in an inert solvent such as benzene, toluene, xylene, hexane, petroleum ether and the like.

The carbene or carbenoid formed as described above immediately gives rise to cyclization selectively with the double bond present in the molecule thereof to produce a 4-oxy-6-alkenyl-bicyclo[3.1.0]hexan-2-one compound of the formula (I) in high yield.

Typical examples of the 4-oxy-6-alkenyl-bicyclo[3.1.0]-hexan-2-one compounds of the formula (I) thus formed are methyl 4-hydroxy-exo-6-(trans-1-peptenyl)-2-oxo-bicyclo[3.1.0]-hexane-1-carboxylate, methyl 4-(1-ethoxyethyloxy)-exo-6-(trans-1-heptenyl)-2-oxo-bicyclo[3.1.0]hexane-1-carboxylate, t-butyl 4-(1-ethoxyethyloxy)-exo-6-(trans-1-heptenyl)-2-oxo-bicyclo[3.1.0]hexane-1-carboxylate, methyl exo-6-(trans-1-heptenyl)-2-oxo-4-(2-tetrahydropyranyloxy)-bicyclo[3.1.0]hexane-1-carboxylate, methyl exo-6-(trans-1-heptenyl)-2-oxo-4-trimethylsilyloxybicyclo[3.1.0]hexane-1-carboxylate, methyl 4-benzyloxy-exo-6-(trans-1- heptenyl)-2-oxo-bicyclo[3.1.0]hexane-1-carboxylate and the like.

The 4-oxy-6-alkenyl-bicyclo[3.1.0]hexan-2-one compounds of the formula (I) obtained as above can then be converted into the corresponding 4-oxycyclopentanone compounds of the formula (IIa) by ring-opening of the cyclopropyl group present in the molecule through a reaction with a mercaptan compound of the formula (VI)

$$R^5—SH \quad (VI)$$

wherein $R^5$ represents an alkyl group having 1 to 4 carbon atoms or an aryl group, in the presence of a base to form a compound of the formula (IIa).

The reaction between a 4-oxy-6-alkenyl-bicyclo[3.1.0]exan-2-one compound (I) and a mercaptan compound (VI) can be carried out at a temperature of about 0° to about 100° C., preferably at room temperature, using preferably an approximately equimolar amount of the mercaptan compound and the compound of the formula (I) in the presence of a base. A larger amount of the mercaptan compound over the equimolar amount can be used without causing any adverse affect.

Suitable examples of bases which can be used in the above reaction are alkali metal hydroxides such as potassium hydroxide, sodium hydroxide and the like, alkali metal alkoxides such as sodium methoxide, potassium methoxide, sodium ethoxide, potassium t-butoxide and the like, and organic amines such as triethylamine, tributylamine, pyridine and the like.

A so-called catalytic amount of the base is generally sufficient, but the use of an approximately equimolar amount of the base relative to the compound of the formula (I) is preferred for reducing the reaction time required for completing the reaction and also increasing the yield of the desired product of the formula (IIa).

The base used in the above reaction is considered to react at the first stage with a mercaptan compound of the formula (VI) in the reaction system to produce a mercaptide anion. The mercaptide anion thus formed appears to attack the bicyclo nucleus of the compound of the formula (I) thereby resulting in a partial ring-opening of the bicyclo nucleus to produce a salt comprising an anion of the compound of the formula (IIa) and the anion is then converted into a compound of the formula (IIa), as illustrated below where an alkali metal hydroxide (MOH, M is an alkali metal) is used as a base.

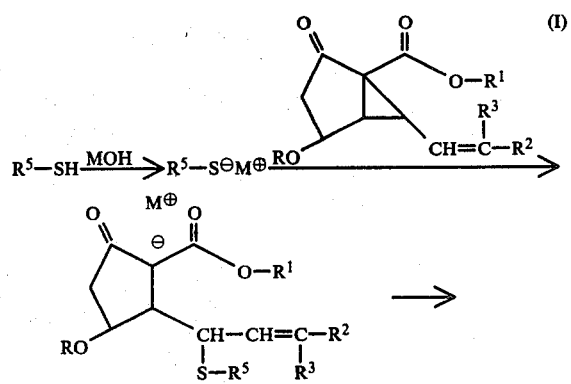

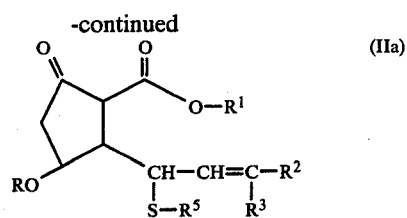

As is apparent to one skilled in the art, a mercaptide anion corresponding to the mercaptan compound of the formula (VI) also has the same function as the mercaptan compound, and thus the present invention also includes the use of such mercaptide anions in the reaction with the compound of the formula (I)

In carrying out the reaction between the 4-oxy-6-alkenylbicyclo[3.1.0]hexan-2-one compound of the formula (I) and the mercaptan compound of the formula (VI), it is preferred to use a polar solvent which does not take part in the reaction and which is inert to the reactants used as well as to the desired product. Suitable examples of polar solvents are ethers such as diethyl ether, tetrahydrofuran and the like, alcohols such as methanol, ethanol, t-butanol and the like, dimethylformamide, acetonitrile, dimethyl sulfoxide and the like.

Representative compounds of the 4-oxycyclopentanone sulfide compounds of the formula (IIa) are methyl 4-hydroxy-2-oxo-5-(1-phenylthio-trans-2-octenyl)-cyclopentane-1-carboxylate, methyl 4-(1-ethoxyethyloxy)-2-oxo-5-(1-phenylthiotrans-2-octenyl)-cyclopentane-1-carboxylate, methyl 2-oxo-5-(1-phenylthio-trans-2-octenyl)-4-trimethylsilyloxy-cyclopentane-1-carboxylate, methyl 4-benzyloxy-2-oxo-5-(1-phenylthiotrans-2-octenyl)-cyclopentane-1-carboxylate and the like.

The compound of the formula (IV) can be prepared from the 4-oxycyclopentanone sulfide compound of the formula (IIa) by protecting the carbonyl group contained in the compound of the formula (IIa) with a protective group for a hydroxy group which is well known in the art.

The protection of the carbonyl group can be achieved by the following procedures:

(a) The carbonyl group can be protected by the reaction of the compound of the formula (IIa) with a diazoalkane having 1 to 4 carbon atoms, for example, diazomethane, diazoethane, diazobutane and the like. Such diazoalkanes can be used in an amount of from about 1 to 3 mols, preferably an equimolar amount relative to the compound of the formula (IIa). The reaction between the 4-oxycyclopentanone sulfide compound (IIa) and a diazoalkane can be advantageously effected at a temperature of about 0° to about 20° C., preferably at room temperature, for about 1 to about 24 hours, in a solvent such as ethers, for example, diethyl ether, tetrahydrofuran and the like, methylene chloride, or a mixture thereof.

(b) The carbonyl group can also be protected by the reaction of the compound of the formula (IIa) with a silylating agent which is capable of introducing a silyl group as a protective group. This silylation reaction can be advantageously achieved using a trialkylchlorosilane such as trimethylchlorosilane, dimethyl i-propylchlorosilane, dimethyl t-butylchlorosilane and the like in an approximately equimolar amount relative to the compound of the formula (II), in the presence of a base.

Suitable examples of the base which can be used in the silylation reaction are organic amines such ethylamine, diethylamine, triethylamine, isopropylamine, n-butylamine, tri-n-butylamine, cyclohexylamine, dimethylaniline, pyrrolidine, piperidine, morpholine, pyridine, quinoline and the like. These organic amines can be used in an approximately equimolar amount relative to the compound of the formula (IIa). Alternatively, the above silylation reaction can be attained by treating the compound of the formula (IIa) with a silylating agent such as hexamethyldisilazane, bistrimethylsilylacetamide and the like.

In either case, the silylation reaction can be preferably conducted in a solvent, for example, ethers such as diethyl ether, tetrahydrofuran, dioxane, dimethyl ether and the like, amides such as dimethylformamide, dimethylacetamide, hexamethylphosphoric triamide and the like, nitriles such as acetonitrile and the like, sulfoxides such as diemthyl sulfoxide and the like, or a mixture thereof. The silylation reaction can be carried out at a temperature of from about −30° C. to about 40° C., preferably at room temperature, for about 10 minutes to about 24 hours.

The compound of the formula (V) can then be prepared from the corresponding compound of the formula (IV) by reduction. This reduction can be carried out using a metal hydride, in particular, a complex metal hydride, as a reducing agent in an amount of about 1 to about 5 mols, preferably an equimolar amount relative to the compound of the formula (IV).

Suitable examples of reducing agents are lithium aluminum hydride, lithium alkoxy aluminum hydrides or sodium alkoxy aluminum hydrides such as lithium tri-tert-butoxy aluminum hydride and the like, and dialkyl aluminum hydrides such as diisobutyl aluminum hydride and the like.

The reduction can be advantageously conducted in a solvent, for example, ethers such as diethyl ether, 1,2-dimethoxyethane, tetrahydrofuran and the like, or hydrocarbons such as benzene, toluene, xylene, hexane and the like, or a mixture thereof, at a temperature of from about −80° C. to room temperature.

The 2-hydroxymethyl compound of the formula (IIb) can be prepared from the corresponding compound of the formula (V) by hydrolysis using, optionally, an acid catalyst. However, when the protective group ($R^6$) is a silyl group, this protective group can be removed simultaneously at the working-up stage of the reduction process described above and, therefore, no specific procedure is required for the removal of the silyl group. When the protective group ($R^6$) is an alkyl group, the compound of the formula (V) can be subjected to hydrolysis using an acid catalyst thereby yielding the compound of the formula (IIb).

Suitable examples of acid catalysts which can be used in the hydrolysis are sulfonic acids such as p-toluenesulfonic acid, methanesulfonic acid and the like, inorganic acids such as hydrochloric acid, sulfuric acid, perchloric acid and the like, ammonium chloride and the like, in a catalytic amount.

Suitable examples of solvents which can be used in the above hydrolysis are water, alcohols such as methanol, ethanol, and the like, ethers such as diethyl ether, 1,2-diethoxyethane, tetrahydrofuran and the like, hydrocarbons such as benzene, toluene, xylene and the like, or a mixture thereof.

The hydrolysis can be carried out at a temperature of about −40° C. to room temperature for about 1 to about 24 hours.

Representative examples of the thus obtained 2-hydroxymethyl compounds of the formula (IIb) are 2-hydroxymethyl-3-(1-phenylthio-trans-2-octenyl)-4-hydroxycyclopentanone, 2-hydroxymethyl-3-(1-phenylthio-trans-2-octenyl)-4-(1-ethoxyethyloxy)-cyclopentanone, 2-hydroxymethyl-3-(1-phenylthio-trans-2-octenyl)-4-(4-trimethylsilyloxy)-cyclopentanone, 2-hydroxymethyl-3-(1-phenylthio-trans-2-octenyl)-4-(4-benzyloxy)-cyclopentanone and the like.

The 2-methylene compounds of the formula (IIc) can be prepared from the corresponding 2-hydroxymethyl compounds of the formula (IIb) by treating the 2-hydroxymethyl compound with a sulfonic acid halide in the presence of a base.

Suitable examples of sulfonic acid halides which can be used in the above treatment are halides of methanesulfonic acid, ethanesulfonic acid, p-toluenesulfonic acid and the like. These sulfonic acid halides can be used in an approximately equimolar amount relative to the 2-hydroxymethyl compound of the formula (IIb).

Suitable examples of bases which can be used in the above treatment of the 2-hydroxymethyl compounds of the formula (IIb) are ethylamine, diethylamine, triethylamine, i-propylamine, n-butylamine, tri-n-butylamine, dimethylaniline, pyrrolidine, piperizine, morpholine, pyridine and the like. These bases can be used in an excess amount so as to serve as solvents, but ethers such as diethyl ether, 1,2-dimethoxyethane, tetrahydrofuran and the like, amides such as dimethylformamide, dimethylacetamide, hexamethylphosphoric triamide and the like, nitriles such as acetonitrile and the like, sulfoxides such as dimethyl sulfoxide and the like can be used as solvents.

The reaction between the 2-hydroxymethyl compound of the formula (IIb) nd a sulfonic acid halide can be carried out at a temperature of about −30° C. to about 40° C. for about 1 to about 24 hours, depending upon the reactivity of the sulfonic acid halide used. The reaction is preferably carried out at room temperature from the standpoint of ease in operation.

This reaction appears to proceed via an intermediate as illustrated below and, therefore, the present invnetion also includes within the scope thereof such intermediates as well as the reaction route through such intermediates.

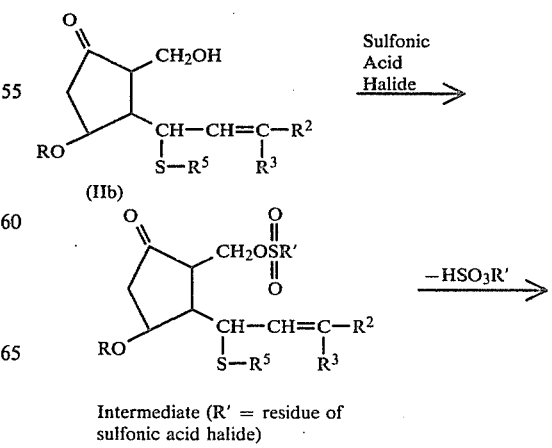

Intermediate (R' = residue of sulfonic acid halide)

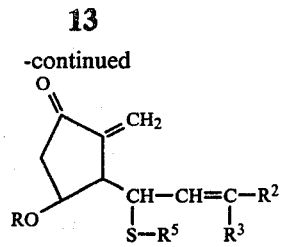

(IIc)

Representative examples of the thus obtained 2-methylene compounds of the formula (IIc) are 2-methylene-3-(1-phenylthio-trans-2-octenyl)-4-hydroxycyclopentanone, 2-methylene-3-(1-phenylthio-trans-2-octenyl)-4-(1-ethoxyethyloxy)-cyclopentanone, 2-methylene-3-(1-phenylthio-trans-2-octenyl)-4-(4-trimethylsilyloxy)-cyclopentanone, 2-methylene-3-(1-phenylthio-trans-2-octenyl)-4-(4-benzyloxy)-cyclopentanone, and the like.

The present invention is further illustrated by the following Reference Examples and Examples, but they are given for illustrative purposes only and are not to be construed as limiting the scope of this invention. Unless otherwise indicated, all parts, percentages, ratios and the like are by weight.

REFERENCE EXAMPLE 1

According to the conventional procedure as described in J. Amer. Chem. Soc., 96, 1082 (1974), a solution of dianion of 3.82 g (33 mmols) of methyl acetoacetate in 60 ml of tetrahydrofuran was prepared. To the above solution cooled at a temperature of $-78°$ C. was added dropwise a solution of 5.0 g (33 mmols) of trans, trans-2,4-decadienal and 5.82 g (33 mmols) of hexamethylphosphoric triamide in 15 ml of tetrahydrofuran. The mixture was then stirred for 3 hours at a temperature of $-78°$ C. and then decomposed with a dilute aqueous hydrochloric acid solution. The organic layer was separated and the aqueous layer was extracted with ethyl acetate. The combined extract and organic layer was washed with a saturated aqueous solution of sodium chloride and dried over anhydrous magnesium sulfate, and the solvent was removed by distillation to obtain methyl 5-hydroxy-3-oxo-trans, trans-6,8-tetradecadienoate as an oily substance.

NMR Absorption Spectrum $(CCl_4)\delta$: 3.33 (s, 2H), 3.67 (s, 3H), 4.5 (m, 1H), 5.1–6.4 (m, 4H).

REFERENCE EXAMPLE 2

1.0 g (3.73 mmols) of methyl 5-hydroxy-3-oxo-trans, trans-6,8-tetradecadienoate and 0.95 g (13.2 mmols of ethyl vinyl ether were mixed and a catalytic amount of phosphorus oxytrichloride was added to the mixture followed by stirring at room temperature for 1 hour. After completion of the reaction, several drops of triethylamine was added to the mixture and the solvent was removed by distillation to obtain methyl 3-oxo-5-(1-ethoxyethyloxy)-trans, trans-6,8-tetradecadienoate as an oily substance in a quantative yield.

Infrared Absorption Spectrum $(cm^{-1})$: 2925, 1755, 1723, 1658, 1630, 1450, 1380, 1330, 1240, 1150, 1130, 1090, 1055, 994.

REFERENCE EXAMPLE 3

In the same manner as described in Reference Example 2 above but using 2-methoxy-1-propane in place of the ethyl vinyl ether, methyl 3-oxo-5-(1-methoxy-1-methylethyloxy)-trans, trans-6,8-tetradecadienoate was obtained in a quantative yield.

NMR Absorption Spectrum $(CCl_4)\delta$: 3.08 (s, 3H), 3.32 (s, 2H), 3.68 (s, 3H), 4.5 (m, 1H), 5.2–6.3 (m, 4H).

Infrared Absorption Spectrum $(cm^{-1})$: 2950, 2925, 1754, 1722, 1656, 1630, 1210, 1145, 1070, 990.

REFERENCE EXAMPLE 4

1.0 g of the compound having the formula (I) wherein R is a 1-ethoxyethyl group, $R^1$ is a methyl group, $R^2$ is an n-pentyl group and $R^3$ is a hydrogen atom was dissolved in 10 ml of a mixture of isopropyl alcohol and water (4:1 by volume) and a catalytic amount of p-toluenesulfonic acid was added to the above solution. The resulting mixture was then allowed to react at a temperature of 40° C. for 24 hours while stirring. After completion of the reaction, a saturated aqueous solution of sodium bicarbonate was added to the reaction mixture and the mixture was extracted with ethyl acetate. The extract was washed with a saturated aqueous solution of sodium chloride, dried over anhydrous magnesium sulfate and filtered. The solvent was removed by distillation and the residue was purified by silica gel column chromatography using a mixture of ethyl acetate and hexane as an eluent to obtain 0.68 g (86% yield) of a compound having the formula (I) wherein R and $R^3$ are hydrogen atoms, $R^1$ is a methyl group and $R^2$ is an n-pentyl group, as a yellow oil.

Infrared Absorption Spectrum $(cm^{-1})$: 3425, 1730, 1440, 1250. Mass Spectrum $(M^+ +1)$: 267.

EXAMPLE 1

A mixture of 7.24 g (21.3 mmols) of methyl 3-oxo-5-(1-ethoxyethyloxy)-trans, trans-6,8-tetradecadienoate, 4.20 g (21.3 mmols) of p-tosyl azide, 2.15 g (21.3 mmols) of triethylamine and 39 ml of acetonitrile was stirred at room temperature for 3 hous. After completion of the reaction, the solvent was removed by distillation and the resulting residue was extracted with diethyl ether. The ethereal extract was washed with a 5% aqueous solution of potassium hydroxide and dried over anhydrous magnesium sulfate. The solvent was removed from the extract by distillation to obtain 7.61 g (98% yield) of methyl 2-diazo-3-oxo-5-(1-ethoxyethyloxy)-trans, trans-6,8-tetradecadienoate.

NMR Absorption Spectrum $(CCl_4)\delta$: 3,80 (s, 3H), 4.60 (m, 2H), 5.0–6.4 (m, 4H).

Infrared Absorption Spectrum $(cm^{-1})$: 2925, 2125, 1728, 1654, 1375, 1313, 1167, 1125, 990.

EXAMPLE 2

A mixture of 1.0 g (2.94 mmols) of methyl 3-oxo-5-(1-methoxy-1-methylethyloxy)-trans, trans-6,8-tetradecadienoate, 0.58 g (2.94 mmols) of p-tosyl azide, 5.3 ml of acetonitrile and 0.30 g (2.94 mmols) of triethylamine was stirred at room temperature for 2.5 hours. The resulting reaction mixture was then worked up in the same manner as described in Example 1 to obtain 0.88 g (89% yield) of methyl 2-diazo-3-oxo-5-(1-methoxy-1-methylethyloxy)-trans, trans-6,8-tetradecadienoate.

NMR Absorption Spectrum $(CCl_4)\delta$: 3.06 (s, 3H), 3.68 (s, 3H), 4.60(q, J=6 Hz, 1H), 5.2–6.4 (m, 4H).

Infrared Absorption Spectrum $(cm^{-1})\delta$: 2950, 2925, 2135, 1730, 1656, 1441, 1319, 1210, 992.

EXAMPLE 3

2.28 g (6.2 mmols) of methyl 2-diazo-3-oxo-5-(1-ethoxyethyloxy)-trans, trans-6,8-tetradecadienoate was dissolved in 127 ml of benzene and 224 mg of acetylacetone copper was added to the solution. The mixture was then heated while refluxing and vigorously stirring for 6 hours. After completion of the reaction, the solvent was removed by distillation and the residue was purified by silica gel column chromatography to obtain 1.55 g (74% yield) of methyl exo-6-(trans-1-heptenyl)-2-oxo-4-(1-ethoxyethyloxy)-bicyclo[3.1.0]hexane-1-carboxylate as an oily substance. The resulting product was found to be a mixture of diastereomers by NMR spectrum.

NMR Absorption Spectrum (CCl$_4$)δ: 3.64(s, 0.9H), 3.67 (s, 2.1H), 4.25(m, 0.7H), 4.5–4.8 (m, 1.3H), 4.9–5.3 (m, 1H), 5.4–5.8 (m, 1H).

Infrared Absorption Spectrum (cm$^{-1}$): 2925, 1760, 1738, 1450, 1363, 1345, 1255, 1228, 1200, 1165, 1148, 1128, 1092, 1055, 972, 931.

EXAMPLE 4

200 mg of methyl 2-diazo-3-oxo-5-(1-ethoxyethyloxy)-trans, trans-6,8-tetradecadienoate was dissolved in 17 ml of n-octane and the solution was heated while refluxing for 10 minutes with vigorous stirring in the presence of 200 mg of copper powder. The reaction mixture was filtered and the filtrate was concentrated. The resulting crude product was purified by silica gel column chromatography to obtain 185 mg (60% yield) of methyl exo-6-(trans-1-heptenyl)-2-oxo-4-(1-ethoxyethyloxy)-bicyclo[3.1.0]hexane-1-carboxylate.

EXAMPLE 5

500 mg of methyl 2-diazo-3-oxo-5-(1-ethoxyethyloxy)-trans, trans-6,8-tetradecadienoate was dissolved in 30 ml of a mixture of benzene and toluene (1:1 by volume), and 250 mg of cupric cyanide was added to the solution. The mixture was then heated while refluxing for 14 hours with vigorous stirring. After completion of the reaction, the solvent was removed by distillation and the resulting residue was purified by silica gel chromatography to obtain methyl exo-6-(trans-1-heptenyl)-2-oxo-4-(1-ethoxyethyloxy)-bicyclo[3.1.0]hexane-1-carboxylate in a 50% yield.

EXAMPLE 6

200 mg of methyl 2-diazo-3-oxo-5-(1-methoxy-1-methylethyloxy)-trans, trans-6,8-detradecadienoate was dissolved in 11 ml of benzene and 20 mg of acetylacetone copper was added to the solution. The mixture was then heated while refluxing for 20 hours with vigorous stirring. After completion of the reaction, the solvent was removed by distillation and the resulting residue was purified by silica gel chromatography to obtain methyl exo-6-(trans-1-heptenyl)-2-oxo-4-(1-methoxy-1-methylethyloxy)-bicyclo[3.1.0]hexane-1-carboxylate. The product thus obtained was found to be a mixture of diastereomers by NMR spectrum.

NMR Absorption Spectrum (CCl$_4$)δ: 3.12 (s, 3H), 3.64 (s, 1H), 3.68 (s, 2H), 4.32 (d, J=5 Hz, 0.7H), 4.5–4.8 (m, 0.3H), 4.9–5.3 (m, 1H), 5.4–5.9 (m, 1H).

EXAMPLE 7

100 mg (0.30 mmol) of methyl exo-6-(trans-1-heptenyl)-2-oxo-4-(1-ethoxyethyloxy)-bicyclo[3.1.0]hexane-1-carboxylate was dissolved in 2 ml of isopropyl alcohol in an argon atmosphere and the solution was cooled to a temperature of −70° C. Separately, a thiophenol solution was prepared by dissolving 40 mg (0.36 mmol) of thiophenol in 2 ml of isopropyl alcohol in an argon atmosphere and adding thereto 40 mg (0.36 mmol) of potassium t-butoxide. The thiophenol solution thus obtained was added dropwise to the above-described solution cooled to −70° C. followed by stirring for 15 minutes. The resulting mixture was allowed to warm slowly to room temperature and then worked up in a usual manner to obtain 90 mg (68% yield) of methyl 2-(1-phenylthio-trans-2-octenyl)-3-(1-ethoxyethyloxy)-5-oxo-cyclopentane-1-carboxylate as a mixture of isomers.

NMR Absorption Spectrum (CCl$_4$)δ: 3.58 (s, 1.5H), 3.65 (s, 0.5H), 3.67 (s, 1H), 4.66 (quintet, J=5 Hz, 1H), 5.25–5.45 (m, 2H), 7.0–7.4 (m, 5H).

Infrared Absorption Spectrum (cm$^{-1}$): 3050, 2950, 2925, 2850, 1766, 1738, 1666, 1625, 1588, 1440, 1370, 1340, 1255, 1132, 1090, 1056, 1027, 750, 693.

EXAMPLE 8

500 mg (1.48 mmol) of methyl exo-6-(trans-1-heptenyl)-2-oxo-4-(1-ethoxyethyloxy)-bicyclo[3.1.0]hexane-1-carboxylate was dissolved in 8 ml of a mixture of t-butyl alcohol and water (4:1 by volume) and 194 ml (1.78 mmol) of thiophenol was added to the solution. A catalytic amount of triethylamine was then added to the mixture while cooling in an ice bath in an argon atmosphere and the mixture was stirred for 25 hours. After completion of the reaction, a saturated aqueous ammonium chloride was added to the mixture which was then extracted with ethyl acetate. The extract was washed with a saturated aqueous sodium chloride and dried over anhydrous magnesium sulfate. The solvent was then removed by distillation and the resulting residue was purified by silica gel column chromatography to obtain 663 mg (57% yield) of methyl 2-(1-phenylthio-trans-2-octenyl)-3-(1-ethoxyethyloxy)-5-oxo-cyclopentane-1-carboxylate as a mixture of isomers.

EXAMPLE 9

0.93 g (2.08 mmols) of methyl 2-(1-phenylthio-trans-2-octenyl)-3-(1-ethoxyethyloxy)-5-oxo-cyclopentane-1-carboxylate was dissolved in 9 ml of anhydrous diethyl ether and 2.0 ml of bis(trimethylsilyl)acetamide was added to the solution while cooling in an ice bath followed by stirring for 1 hour. After completion of the reaction, the solvent was removed by distillation under reduced pressure to obtain a compound of the formula (IV) wherein R is a 1-ethoxyethyl group, $R^2$ is an n-pentyl group, $R^1$ is a methyl group, $R^6$ is a trimethylsilyl group, $R^3$ is a hydrogen atom and $R^5$ is a phenyl grop, as an oily substance in a quantitative yield.

NMR Absorption Spectrum (CCl$_4$)δ: 0.23 (s, 6H), 3.61 (s, 3H), 4.70 (m, 1H), 5.4 (m, 2H), 7.16 (bs, 5H).

EXAMPLE 10

2.08 mmols of the compound obtained in Example 9 above was dissolved in 10 ml of anhydrous toluene and the solution was cooled to −78° C. To the solution was added dropwise 9.3 ml of a solution of diisobutyl aluminum hydride (10 mmols) in n-hexane in an argon atmosphere. After stirring the mixture for 30 minutes, 3.8 ml of methanol was added to the reaction mixture and the resulting mixture was allowed to warm to room temperature. The precipitate formed was removed by filtration and the filtrate was washed with a saturated aqueous solution of sodium chloride and dried over anhydrous magnesium sulfate. The solvent was then removed from the filtrate by distillation to obtain a compound of the formula (IIb) wherein $R^5$ is a phenyl group, R is a 1-ethoxyethyl, $R^2$ is an n-propyl group and $R^3$ is a hydrogen atom in a 90% yield.

NMR Absorption Spectrum (CCl₄)δ: 4.7 (m, 1H), 5.28 (m, 2H), 7.20 (bs, 5H).

EXAMPLE 11

2.08 mmols of the compound obtained in Example 10 above was dissolved in 17 ml of anhydrous pyridine and 1.3 ml of methanesulfonic acid chloride was added to the solution while cooling in an ice bath followed by stirring for 3.5 hours. Water was added to the resulting reaction mixture which was then extracted with ethyl acetate. The extract was washed with a saturated aqueous solution of sodium chloride and dried over anhydrous magnesium sulfate. The solvent was removed by distillation and the resulting oily substance was dissolved in 10 ml of anhydrous tetrahydrofuran and 0.4 ml of triethylamine was added to the solution followed by stirring for 1.5 hours at room temperature. The solvent was then removed by distillation under reduced pressure and the resulting oily substance was purified by silica gel column chromatography to obtain a compound of the formula (IIc) wherein $R^5$ is a phenyl group, R is a 1-ethoxyethyl group, $R^2$ is an n-pentyl group and $R^3$ is a hydrogen atom, in a 90% yield as a light yellow oily substance.

Infrared Absorption Spectrum (cm⁻¹): 2920, 1730, 1638, 1583, 1440, 1385, 1340, 1256, 1125, 1090, 1055, 1025, 955, 748, 691.

Mass Spectrum: M⁺ 402 (Calculated Value: 402)

Elementary Analysis: Calc'd: C, 71.60; H, 8.51. Found: C, 71.43; H, 8.43.

NMR Absorption Spectrum (CCl₄)δ: 4.28 1 (m, 1H), 4.69 (m, 1H), 5.25 (m, 2H), 5.66 (m, 1H), 6.12 (m, 1H), 7.1–7.5 (m, 5H).

While the invention has been described with reference to specific embodiments thereof, it will be apparent to one skilled in the art that various modifications and changes can be made therein without deaprting from the spirit and the scope thereof.

What is claimed:

1. A 4-oxycyclopentanone compound represented by the formula (II)

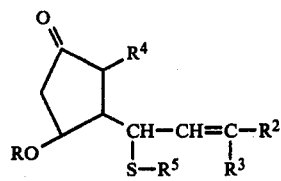

wherein R represents a hydrogen atom or a protective group for a hydroxy group, $R^2$ represents a substituted or unsubstituted alkyl group having 1 to 8 carbon atoms, $R^3$ represents a hydrogen atom or an alkyl group having 1 to 4 carbon atoms, $R^4$ represents a hydroxymethyl group, a methylene group ($=CH_2$) or a $-COOR^1$ group wherein $R^1$ represents an alkyl group having 1 to 4 carbon atoms or an aryl group, and $R^5$ represents an alkyl group having 1 to 4 carbon atoms or an aryl group.

2. Methyl 4-hydroxy-2-oxo-5-(1-phenylthio-trans-2-octenyl)-cyclopentane-1-carboxylate according to claim 1.

3. Methyl 4-(1-ethoxyethyloxy)-2-oxo-5-(1-phenylthio-trans-2-octenyl)-cyclopentane-1-carboxylate according to claim 1.

4. Methyl 2-oxo-5-(1-phenylthio-trans-2-octenyl)-4-trimethylsilyloxy-cyclopentane-1-carboxylate according to claim 1.

5. Methyl 4-benzyloxy-2-oxo-5-(1-phenylthio-trans-2-octenyl)-cyclopentane-1-carboxylate according to claim 1.

6. 2-Hydroxymethyl-3-(1-phenylthio-trans-2-octenyl)-4-hydroxycyclopentanone according to claim 1.

7. 2-Hydroxymethyl-3-(1-phenylthio-trans-2-octenyl)-4-(1-ethoxyethyloxy)-cyclopentanone according to claim 1.

8. 2-Hydroxymethyl-3-(1-phenylthio-trans-2-octenyl)-4-(4-trimethylsilyloxy)-cyclopentanone according to claim 1.

9. 2-Hydroxymethyl-3-(1-phenylthio-trans-2-octenyl)-4-(4-benzyloxy)-cyclopentanone according to claim 1.

10. 2-Methylene-3-(1-phenylthio-trans-2-octenyl)-4-hydroxycyclopentanone according to claim 1.

11. 2-Methylene-3-(1-phenylthio-trans-2-octenyl)-4-(1-ethoxyethyloxy)-cyclopentanone according to claim 1.

12. 2-Methylene-3-(1-phenylthio-trans-2-octenyl)-4-(4-trimethylsilyloxy)-cyclopentanone according to claim 1.

13. 2-Methylene-3-(1-phenylthio-trans-2-octenyl)-4-(4-benzyloxy)-cyclopentanone according to claim 1.

* * * * *